United States Patent [19]

Urquhart et al.

[11] Patent Number: 4,649,043

[45] Date of Patent: * Mar. 10, 1987

[54] DRUG DELIVERY SYSTEM FOR DELIVERING A PLURALITY OF TINY PILLS IN THE GASTROINTESTINAL TRACT

[75] Inventors: John Urquhart, Palo Alto; Felix Theeuwes, Los Altos, both of Calif.

[73] Assignee: ALZA Corporation, Palo Alto, Calif.

[*] Notice: The portion of the term of this patent subsequent to Feb. 28, 2001 has been disclaimed.

[21] Appl. No.: 571,299

[22] Filed: Jan. 16, 1984

Related U.S. Application Data

[63] Continuation of Ser. No. 360,477, Mar. 22, 1982, Pat. No. 4,434,153.

[51] Int. Cl.$^4$ .......................... A61K 9/22; A61K 9/26
[52] U.S. Cl. ..................................... 424/469; 424/486
[58] Field of Search ....................... 424/16, 19, 22, 20, 424/21, 81

[56] References Cited

U.S. PATENT DOCUMENTS

| 2,996,431 | 8/1961 | Barry | 424/20 |
| 3,390,050 | 6/1968 | Speiser | 424/19 |
| 3,867,518 | 2/1975 | Michaels | 424/19 |
| 4,167,558 | 11/1979 | Sheth et al. | 424/22 |
| 4,178,361 | 12/1979 | Cohen et al. | 424/22 |

FOREIGN PATENT DOCUMENTS 1182124  2/1970  United Kingdom .

OTHER PUBLICATIONS

The Theory and Practice of Industrial Pharmacy 2nd Edition, Lea & Febiger 1976.

Primary Examiner—Shep k. Rose
Attorney, Agent, or Firm—Paul L. Sabatine; Edward L. Mandell; Steven F. Stone

[57] ABSTRACT

A delivery device is disclosed for delivering a beneficial drug to a biological environment of use. The device comprises a hydrogel reservoir containing tiny pills. The tiny pills comprise a wall surrounding a drug core.

5 Claims, 4 Drawing Figures

DRUG DELIVERY SYSTEM FOR DELIVERING A PLURALITY OF TINY PILLS IN THE GASTROINTESTINAL TRACT

CROSS-REFERENCE TO RELATED APPLICATIONS

This application is a continuation of Ser. No. 06/360/477 filed on Mar. 22, 1982, and now U.S. Pat. No. 4,434,153, issued on Feb. 28, 1984.

FIELD OF THE INVENTION

This invention pertains to a drug delivery system manufactured in the form of a drug delivery device. More particularly, the invention pertains to a drug delivery device for remaining in the stomach over a prolonged period of time, and it comprises a reservoir formed of an expandable material containing a plurality of tiny pills.

BACKGROUND OF THE INVENTION

A long-felt need exists for a drug delivery system for remaining in the stomach over a prolonged period of time. The need exists for a drug delivery system that remains in the stomach and acts as an in vivo reservoir that releases drug at a controlled rate and continuously for (a) absorption in the stomach, or for (b) passage into the intestine for absorption therein. Drug delivery systems are used clinically for administering a drug for its beneficial effect. Often the drug is administered from (1) a delivery system that releases a drug as the system moves through the gastrointestinal tract over time, or from (2) a delivery system that remains in the stomach and releases drug while in the stomach. The delivery systems are used because they eliminate the need for administering a number of single doses at periodic intervals. The convenience of using a drug delivery system, which releases drug over a prolonged period of time as opposed to the administration of a number of doses, has long been recognized in the practice of medicine. The preferred sought-after therapeutic advantage to the patient and the clinician is controlled and optimum blood levels of drug during the period of time drug is released from the delivery system. This advantage arises from the delivery system continuously supplying drug for its passage and absorption into the blood for replacing drug used, eliminated, or metabolically inactivated by the patient.

The above presentation teaches that delivery systems have been provided for continuously supplying drug for obtaining better therapy in the management of health and disease. For example, one system used for continuously releasing drug over a long period of time is disclosed by patentee Blythe in U.S. Pat. No. 2,738,303. The delivery system disclosed in this patent consists essentially of a capsule containing uncoated pellets of drug and coated pellets of drug having varying thickness. On their release from the capsule, the uncoated pellets provide an initial amount of drug and the coated pellets provide drug over a period of time. Another delivery system is disclosed by patentees Sheth et al in U.S. Pat. Nos. 4,140,775 and 4,167,558. The systems disclosed in these latter patents consists essentially of a tablet formed of a compressed polymer containing dispersed drug. The system is hydrodynamically balanced for remaining in the stomach for releasing drug therein over time.

While the above delivery systems are designed for providing a continuous supply of drug, there are inherent short-comings associated with these delivery systems. For example, pellets often pass through the gastrointestinal tract quickly, and this tends to limit their supplying of drug needed for maintaining a desired blood level of drug. Also, pellets are not designed for remaining in the stomach over an extended period of time as they tend to empty from the stomach in a first order manner like liquids. The tablet, on its exposure to stomach fluid, releases drug by uncontrolled leaching action and at a declining rate, which actions restrict the use of the tablet as a controlled delivery system during the time of its residency in the stomach.

It will be appreciated by those versed in the drug dispensing art in view of the above presentation, that if a delivery system is provided that remains in the stomach and acts as an in vivo drug reservoir while concurrently releases drug in the stomach for (a) absorption in the stomach, or for (b) passage into the intestine for absorption therein, essentially without disrupting the normal emptying of ingested foods and liquids, such a delivery system would have a positive value and represent a substantial contribution to the dispensing art. Likewise, it will be appreciated by those skilled in the art, that if a delivery system is made available that remains in the stomach for releasing drug at a controlled rate over time for achieving therapeutic blood levels, such a delivery system would be clinically useful in the practice of medicine.

OBJECTS OF THE INVENTION

Accordingly, in view of the above presentation it is an immediate object of this invention to provide a novel and useful drug delivery system that satisfies the long-felt need and overcomes the short-comings known to the prior art.

Another object of the invention is to provide a drug delivery device that is simple in construction and which device exhibits all of the practical benefits of controlled and continuous administration of drug to animals and humans over a prolonged period of time.

Another object of the invention is to provide a drug delivery system manufactured in the form of a drug delivery device for prolonged residency in the stomach for executing a therapeutic program therein.

Still another object of the invention is to provide a drug delivery device comprising a reservoir formed of an expandable material containing tiny pills, which device is useful for maintaining the stomach in the fed mode and/or for concomitantly keeping the housekeeper away for extending the stomach residence of the drug delivery device.

Yet another object of the invention is to provide a drug delivery device comprising a swellable reservoir containing tiny pills for remaining in the stomach an extended period of time for making a drug available therein, or for its subsequent passage into the intestine.

Yet still another object of the invention is to provide a drug delivery device that by its size will be retained in the stomach during the fed mode, and prior to its passage into the small intestine bioerodes in the stomach over time.

Yet still another object of the invention is to provide a drug delivery device dimensioned to be retained in the stomach for delivering drug in the stomach and hence into the intestine.

These objects, as well as other objects, features and advantages of the invention, will become more apparent from the following detailed description of the invention, the drawings, and the accompanying claims.

BRIEF DESCRIPTION OF THE DRAWINGS

In the drawings, which are drawn to scale, but are set forth to illustrate various embodiments of the invention, the figures are as follows.

In the drawings and specifications, like parts in related Figures are identified by like numbers. The terms appearing earlier in the specification and in the description of the drawings as well as embodiments thereof, are further described elsewhere in the disclosure.

DETAILED DESCRIPTION OF THE DRAWINGS

Figure 1:
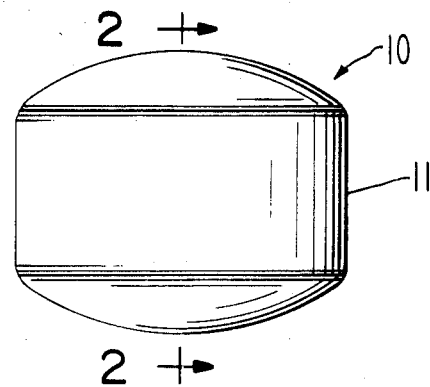
FIG. 1 is a view of an oral drug delivery device provided by the invention.
Figure 2:
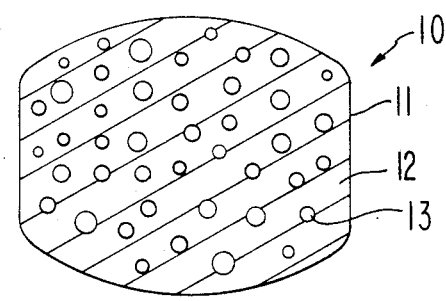
FIG. 2 is an opened view in cross-section through 2—2 of FIG. 1.
Figure 3:
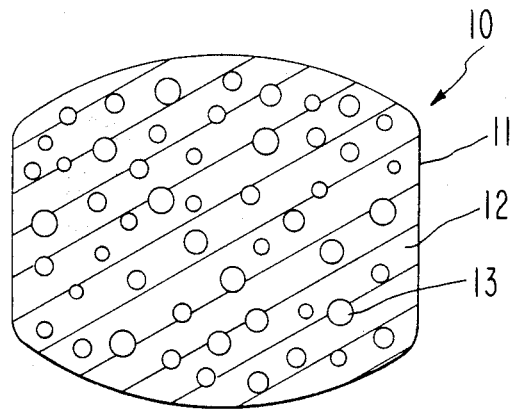
FIG. 3 is an expanded, swelled view of FIG. 2.

Turning now to the drawings in detail, which are an example of various drug delivery device provided by the invention, and which example is not to be construed as limiting, one example of a drug delivery device is seen in FIGS. 1 through 3, considered together, and indicated by numeral 10. In FIGS. 1 through 3, device 10 is seen comprising a body 11 that is adapted, shaped and sized for oral admittance into the gastrointestional tract for extended residency in the stomach. In FIGS. 2 and 3, seen in opened section, body 11 comprises a reservoir 12 formed of a non-toxic material that expands and swells in the presence of fluid in the environment of use, such as water or gastric fluid. The material forming reservoir 12 in a presently preferred embodiment is a hydrophilic polymer, such as a hydrogel. In FIG. 2, reservoir 12 made of a hydrophilic material is illustrated in a non-hydrated state. In FIG. 3 reservoir 12 is illustrated in an enlarged state as the material absorbs and imbibs fluid from the environment of use and swells or expands to some equilibrium state. This increase in size acts as a means for retaining device 10 in the stomach over an extended period of time. Reservoir 12 leaves the environment of use by hydrolyzing or bioeroding during and at the end of the drug delivery period. A description of materials useful for forming reservoir 12 appears later in the specification.

Figure 4:
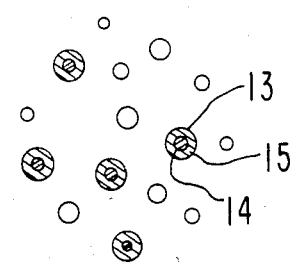
FIG. 4 depicts a multiplicity of tiny pills, some in cross-section on the release from the delivery device of FIGS. 1 to 3.

Drug delivery device 10 of FIGS. 1 through 3, seen in opened view in FIGS. 2 and 3, houses a multiplicity of tiny pills 13 for the controlled delivery of drug over time. In FIG. 4, tiny pills 13 are seen in detail, and they comprise a core of drug 14 surrounded by a wall 15 formed of a release rate controllling material. Tiny pills 13 can have wall 15 made from a material that releases drug 13 in the stomach, or tiny pill 13 can have a wall 15 made from an enteric material which prevents release of drug 14 in the stomach, but will release drug 14 in the intestine. Additionally, the materials forming wall 15 can be selected from materials that release drug 14 by different physical-chemical mechanisms. These mechanisms include erosion, diffusion, osmosis, metabolism, and the like. Wall 15 can have various thicknesses as an additional aid for providing timed release of drug. A description of wall forming materials appears later in the specification.

In operation, device 10 resides in the stomach for an extended period of time by concurrently (1) enlarging in the stomach, and by (2) keeping the stomach in the fed mode. Device 10 delivers drug 14 (a) in the stomach by nonenteric coated tiny pills 13 releasing drug over time, and (b) in the intestine by device 10 releasing enteric coated tiny pills 13 for their passage into the intestine wherein tiny pills 13 deliver drug 14 over a prolonged period of time.

DETAILED DESCRIPTION OF THE INVENTION

In accordance with the practice of the invention, delivery device 10 can be made with a reservoir 12 of a material that does not adversely affect drug 14, an animal or other host. The presently preferred materials useful for forming reservoir 12 comprise hydrogels that exhibit the ability to swell in water and retain a significant fraction of water within its structure. The hydrogels can be noncross-linked or they may be cross-linked with acid mobile covalent or ionic bonds sensitive to slow acidic hydrolysis. The hydrogels can be of plant or animal origin, hydrogels prepared by modifying naturally occuring structures, and synthetic polymeric hydrogels. The polymeric hydrogels swell or expand to a very high degree, usually exhibiting a 2 to 50 fold volume increase. Hydrophilic polymeric materials useful for the purpose include poly(hydroxyalkyl methacrylate), poly(electrolyte complexes), poly(vinyl acetate) cross-linked with hydrolysable bonds, water-swellable N-vinyl lactams polysaccharides, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum crossed-linked with a polyol such as propylene glycol, and the like.

Other hydrogels include hydrophilic hydrogels known as Carbopol ® acidic carboxy polymer, Cyanamer ® polyacrylamides, Good-rite ® polyacrylic acid, polyethylene oxide, starch graft copolymers, Aqua-Keeps ® acrylate polymer, ester cross-linked polyglucan, and the like. The hydrogels are known to the prior art in U.S. Pat. Nos. 3,640,741; 3,865,108; 3,992,562; 4,002,173; 4,014,335; and 4,207,893; and in *Handbook of Common Polymers*, by Scott and Roff, published by the Chemical Rubber Company; Cleveland, Ohio.

Wall 15 of tiny pill 13 surrounding drug 14 can be a wall-forming composition consisting essentially of a fatty ester mixed with a wax, such as a triglyceryl ester selected from the group consisting of glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glyceryl monodecenoate, glyceryl didecenoate and glyceryl tridecenoate.

The wax included in the wall forming composition is a member selected from the group consisting essentially of beeswax, cetyl palmitate, spermacetic wax, carnauba wax, cetyl myristate, cetyl palmitate, ceryl cerotate, stearyl palmitate, stearyl myristate and lauryl laurate.

The composition comprising the ester and the wax can be coated around the drug by using an organic solvent such as a member selected from the group consisting of carbon tetrachloride, chloroform, trichloroethylene, ether, benzene, ethyl acetate, methyl ethyl ketone, isopropyl alcohol, and the like. The fatty esters, waxes, solvents and procedures for making tiny pills that slowly disintegrate and continuously provide drug over a period of 10 to 12 hours are disclosed in U.S. Pat. No. 2,793,979.

Wall 15 of tiny pills 13 in another embodiment is formed of an osmotic wall forming material that releases drug 14 at a controlled rate by the process of osmotic bursting over time. Drug 14 in this embodiment is present in the form of an osmotic solute, such as a therapeutically acceptable salt, and it exhibits an osmotic pressure gradient across wall 15 against an external fluid. The membrane material used to form wall 15 are those permeable to the passage of an external fluid and substantially impermeable to the passage of drug. Typical materials include a member selected from the group consisting of cellulose acylate, cellulose diacylate, cellulose triacylate, cellulose acetate, cellulose diacetate, cellulose triacetate, cellulose acetate having a degree of substitution, D.S., up to 1 and an acetyl content of 21%, cellulose diacetate having a D.S. of 1 to 2 and an acetyl content of 21 to 35%, cellulose triacetate having a D.S. of 2 to 3 and an acetyl content of 35 to 44.8%, cellulose acetyl propionate, cellulose acetate butyrate, and the like. The osmotic wall can be coated around the drug in varying thickness by pan coating, spray-pan coating, Wurster fluid air-suspension coating and the like. The wall is formed using organic solvents, including those mentioned above, and solvent systems such as methylene chloride-methanol, methylene chloride-acetate, methanol-acetone, ethylene dichloride-acetone, and the like. Osmotic wall forming material, procedures for forming the wall, and osmotic bursting procedures are disclosed in U.S. Pat. Nos. 2,799,241; 3,952,741; 4,014,334; and 4,016,880.

Wall 15 in another embodiment can be made of a drug release rate controlling material. That is, drug 14 dissolves in the wall and passes through the wall at a controlled rate over time. Exemplary materials useful for forming a diffusional wall include ethylene-vinyl acetate, ethyl cellulose, polyethylene, cross-linked polyvinyl pyrrolidone, vinylidene chloride-acrylonitrile copolymer, polypropylene, silicone, and the like. The wall can be applied by the techniques described above, and materials suitable for forming wall 15 are described in U.S. Pat. Nos. 3,938,515; 3,948,262; and 4,014,335.

Wall 15 in still another embodiment can be made of a bioerodible material that bioerodes at a controlled rate and releases drug 14 to the biological environment of use. Bioerodible materials useful for forming wall 15 include polyvalent acid or alkali mobile cross-linked polyelectrolytes, polycarboxylic acid, polyesters, polyamides, polyimides, polylactic acid, polyglycolic acid, polyorthosesters, and polyorthocarbonates. The polymers and procedures for forming wall 15 are disclosed in U.S. Pat. Nos. 3,811,444; 3,867,519; 3,888,975; 3,971,367; 3,993,057; and 4,138,344.

In the specification and the accompanying claims the term drug includes pharmacologically active substances that produce a local or systemic effect in animals, which term includes warm-blooded mammals such as humans. The active drug that can be delivered includes drugs that act on the central nervous system, depressants, hypnotics, sedatives, psychic energizers, tranquilizers, anticonvulsants, muscle relaxants, antiparkinson agents, analgesics, anti-inflammatory, hormonal agents, contraceptives, sympathomimetics, diuretics, anti-parasites, neoplastics, hypoglycemics, ophthalmics, electrolytes, cardiovascular drugs, and the like.

Exemplary drugs that are soluble in water and can be delivered by the devices of this invention include prochlorperazine edisylate, ferrous sulfate, aminocaproic acid, potassium chloride, mecamylamine hydrochloride, procainamide hydrochloride, amphetamine sulfate, benzhetamine hydrochloride, isoproternol sulfate, methamphetamine hydrochloride, phenmetrazine hydrochloride, betanechol chloride, methacholine chloride, atropine sulfate, methascopolamine bromide, isopropamide iodide, tridihexethyl chloride, oxprenolol hydrochloride, metoprolol hydrochloride, cimetidine hydrochloride, and the like.

Exemplary drugs that have limited solubility in water and can be delivered by devices of this invention include meclizine hydrochloride, phenoxybenzamine, thiethylperazine maleate, anisindone, erythrityl titranitrate, dizoxin, reserpine, acetazolamide, methazolamide, bendroflumethiazide, chlorpropamide, tolazamide, chlormadinone acetate, aluminum aspirin, methotrexate, acetyl sulfisoxazole, erythromycin, progestins, estroginie, progestational, corticosteroids, and the like.

Examples of other drugs that can be delivered by the devices include aspirin, indomethacin, naproxen, fenoprofen, sulidac, diclofenac, indoprofen, propranolol, metoprolol, oxprenolol, timolol, clonidine, theophylline, ferrous lactate, phenoxybenzamine, baclofen, furosemide, and the like. The beneficial drugs are known in the art in *Pharmaceutical Sciences*, by Remington, 14th Ed., 1979, published by Mack Publishing Co.; *The Drug, The Nurse, The Patient, Including Current Drug Handbook*, by Falconer et al., 1974–1976, published by Saunder Company; and *Medicinal Chemistry*, 3rd Ed., Vol. 1 and 2, by Burger, published by Wiley-Interscience Co.

The drug can be present in the tiny pill in various forms, such as unchanged molecules, molecular complexes, therapeutically acceptable salts such as hydrochlorides, hydrobromides, sulfates, oleates, and the like. For acid drugs, salts of metals, amines, or organic cations, quaternary ammonium salts can be used. Derivatives of drugs such as esters, ethers and amides can be used. Also, a drug that is water insoluble can be used in a form that is the water soluble derivative thereof to serve as a solute, and on its release from the device, is converted by enzymes, hydrolyzed by body pH, or other metabolic processes to the original biologically active form. The amount of drug present in a tiny timed pill generally is about 10 ng to 20 mg, and the number of tiny pills in an oral device is about 10 to 1000, preferably 100 to 150. The tiny pills comprising the wall and inner core of drug have a diameter of at least 100 microns and in a presently preferred embodiment a diameter of at least 2000 microns. For oral use, the delivery device comprising the reservoir and the tiny pills homogenously or heterogenously housed therein, can have conventional shapes such as round, oval and the like. The device can have a diameter of 3/16 inches to ½ inches and the like.

The following examples will further serve to illustrate the invention. An orally administrable tablet containing tiny pills of a sympathomimetic drug is prepared as follows: powdered drug is mixed with sucrose and the blend passed through a 15 to 30 mesh screen to yield a multiplicity of cores of drug. Then, a wall-forming composition comprising 85% glycerol monostearate and 15% beeswax in warm carbon tetrachloride is sprayed over cores in a revolving coating pan until a wall is formed that individually surrounds the cores. Next, after the coating is stripped from the tiny pills, a series of oral tablets are prepared by blending about 50 tiny pills with about 200 mg of ground reservoir forming carboxy-vinyl polymer, commercially available as Carbopol ® polymer, and then pressing the latter blend in a tableting machine under a pressure of 4 kg to yield the delivery device.

Additional drug delivery devices are provided by coating a drug core, for example, procainamide hydrochloride, in a fluid air suspension machine with a composition of ethylcellulose in ethanol to surround the drug with a wall of procainamide hydrochloride, yielding tiny pills thereof. After the solvent is vacuum stripped from the tiny pills, they are blended with ground lightly crosslinked polyacrylamide and pressed into an oral tablet.

The above manufacture can be repeated by replacing the ethylcellulose and ethanol with cellulose acetate having an acetyl content of 32% and methylene chloride-methanol solvent; or by applying a bioerodible wall of poly(2,2-dioxotrans-1,4-cyclohexane dimethylene tetrahydrofuran) around the tiny pills. The latter polymer is applied by heating the polymer to 80°-90° C. and then dispersing the tiny pills in the polymer.

In another example, a delivery device is made by first preparing sustained release tiny pills by blending 400 ml of ethyl cellulose-water, 70:30%, solution, 7.5% w:v, with 375 g of theophylline, 150 g of mannitol and 475 g of magnesium stearate and the blend kneaded and passed through an extrusion granulation machine. After drying at 115°-120° F., the cores are passed through a 20 mesh screen and coated with a wall of ethyl cellulose in an air suspension machine to yield tiny timed pills. Next, a multiplicity of tiny pills are blended with a hydrogel reservoir forming polymer consisting essentially of a coherent meshwork that imbibs and immobilizes water, powdered alginate gum crossed-link with propylene glycol, and the mixture is compressed in a tablet machine using 11/32 inch deep concave punch to yield the drug delivery device for orally administering as a bronchodilator in the management of status asthmaticus, and as a pulmonary vasodilator and smooth muscle relaxant. Other forms of theophylline can be used in the subject delivery device such as theophylline sodium acetate, theophylline sodium glycinate, [7-(2,3-dihydroxypropyl)]theophylline, theophylline meglumine and theophylline monoethanolamine.

Other drug delivery systems are made by spraying non-pareil cores with an edible adhesive and then dusting with drug. The drug-coated core is coated with an appropriate number of edible enteric coatings to give enteric coated tiny pills. The number of enteric coats is variable, usually at least 1 to 10 separate coats are used for the present purpose. Finally, the tiny pills are housed in the hydrogel reservoir. Manufacturing procedures for the tiny pill are taught in U.S. Pat. No. 3,365,365. Also, the tiny pills can be made from a core of carbohydrate, such as sucrose, dusted wit with a mixture of talc, starch and galactose, moistened with distilled or deionized water, and then dusted with the desired medicinal, such as the antibiotic erythromycin. The pills are dried and then coated with an outer layer of a non-toxic, acidic, enteric wall formerly selected from the group consisting of keratin, calcium alginate, shellac, partially hydrolyzed styrene-maleic acid copolymer, polyvinylacitate phthalate, polyvinyl hydrogenphthalate, and the like. Finally, the tiny pills are dispersed in a hydrogel reservoir matrix sized, shaped and adapted for oral admittance into the gastrointestinal tract. Procedures for manufacturing the tiny pills are disclosed in U.S. Pat. No. 3,081,233.

It will be appreciated by those versed in the art, the present invention makes available novel and useful delivery devices for dispensing a beneficial drug over a prolonged period of time. Also, it will be understood by those knowledged in the dispensing art, that many embodiments of this invention can be made without departing from the spirit and scope of the invention, and the invention is not to be construed as limited, as it embraces all equivalents therein.

We claim:

1. An orally administrable dispensing device shaped and adapted for oral admittance into the gastrointestinal tract for extended residency in the stomach of the gastrointestinal tract as an in vivo reservoir for the controlled delivery of a beneficial, orally administrable drug to the gastrointestinal tract for executing a therapeutic program in the gastrointestinal tract, the dispensing device comprising:
   (1) a matrix comprising a pharmaceutically acceptable non-toxic, non-hydrated polyethylene oxide that exhibits the ability to retain fluid within its polyethylene oxide structure, absorb fluid from the gastrointestinal tract, and expand with at least a 2 fold volume increase for retaining the dispensing device in the stomach over an extended period of time;
   (2) a plurality of tiny pills dispensed throughout said matrix comprising the polyethylene oxide, the tiny pills comprising:
      (a) a dosage amount of a beneficial orally administrable drug; and
      (b) a wall comprising a release rate controlling composition comprising a cellulosic polymer that surrounds the dosage amount of drug; and,
   (3) wherein, when the dispensing device is in the gastrointestinal tract fluid environment of use, the device executes the therapeutic program for imparting a beneficial effect by (c) tiny pills delivering drug in the stomach for absorption in the stomach and for passage into the intestine for absorption in the intestine, and by (d) the matrix comprising polyethylene oxide releasing tiny pills for tiny pills passing into the intestine with the tiny pills delivering drug over a prolonged period of time.

2. An orally administrable dispensing device shaped and adapted for oral admittance into the gastrointestinal tract for extended residency in the stomach of the gastrointestinal tract as an in vivo reservoir for the controlled delivery of a beneficial orally administrable drug to the gastrointestinal tract for executing a therapeutic program in the gastrointestinal tract, the dispensing device comprising:
   (1) a matrix comprising a pharmaceutically acceptable non-toxic, non-hydrated carboxy polymer that exhibits the ability to retain fluid within its carboxy polymer structure, absorb fluid from the gastrointestinal tract, and expand with at least a 2 fold volume increase for retaining the dispensing device in the stomach over an extended period of time;

(2) a plurality of tiny pills dispersed throughout said matrix comprising the carboxy polymer, the tiny pills comprising:
  (a) a dosage amount of a beneficial orally administrable drug; and,
  (b) a wall comprising a release rate controlling composition comprising a cellulosic polymer that surrounds the dosage amount of drug; and,
(3) wherein, when the dispensing device is in the gastrointestinal tract fluid environment of use, the device executes the therapeutic program for imparting a beneficial effect by (c) tiny pills delivering drug in the stomach for absorption in the stomach and for passage into the intestine for absorption in the intestine, and by (d) the matrix comprising the carboxy polymer releasing tiny pills for passing into the intestine with the tiny pills delivering drug over a period of time.

3. An orally administrable dispensing device comprising:
  (1) a body adapted and shaped for oral admittance into the gastrointestinal tract for extended residency in the stomach of the gastrointestinal tract as an in vivo reservoir for the controlled delivery of a beneficial orally administrable drug to the gastrointestinal tract for executing a therapeutic program in the gastrointestinal tract, said body comprising:
  (2) a pharmaceutically acceptable non-toxic, non-hydrated polyacrylic acid that exhibits the ability to retain fluid within its polyacrylic acid structure, absorb fluid from the gastrointestinal tract, and expand with at least a 2 fold volume increase for retaining the dispensing device in the stomach over an extended period of time;
  (3) a plurality of tiny pills dispersed throughout said body comprising the polyacrylic acids the tiny pills comprising:
    (a) a dosage amount of a beneficial orally administrable drug; and,
    (b) a wall comprising a release rate controlling composition comprising a cellulosic polymer that surrounds the dosage amount of drug; and,
  (4) wherein, when the dispensing device is in the gastrointestinal tract fluid environment of use, the device executes the therapeutic program for imparting a beneficial effect by (c) tiny pills delivering drug in the stomach for absorption in the stomach and for passage into the intestine for absorption in the intestine, and by (d) the body comprising the polyacrylic acid releasing tiny pills for passing into the intestine with the tiny pills delivering drug over a period of time.

4. An orally administrable dispensing device comprising:
  (1) a body adapted and shaped for oral admittance into the gastrointestinal tract for extended residency in the stomach of the gastrointestinal tract as an in vivo reservoir for the controlled delivery of a beneficially orally administrable drug to the gastrointestinal tract for executing a therapeutic program in the gastrointestinal tract, said body comprising:
  (2) a pharmaceutically acceptable non-toxic, non-hydrated polyacrylamide that exhibits the ability to retain fluid within its polyacrylamide structure, absorb fluid from the gastrointestinal tract, and expand with at least a 2 fold volume increase for retaining the dispensing device in the stomach over an extended period of time;
  (3) a plurality of tiny pills dispersed throughout said body comprising the polyacrylamide, the time pills comprising:
    (a) a dosage amount of a beneficial orally administrable drug; and,
    (b) a wall comprising a release rate controlling composition comprising a cellulosic polymer that surrounds the dosage amount of drug; and,
  (4) wherein, when the dispensing device is in the gastrointestinal tract fluid environment of use, the device executes the therapeutic program for imparting a beneficial effect by (c) tiny pills delivering drug in the stomach for absorption in the stomach and for passage into the intestine for absorption in the intestine, and by (d) the body comprising the polyacrylamide releasing tiny pills for passing into the intestine with the tiny pills delivering drug over a period of time.

5. An orally administrable dispensing device comprising:
  (1) a body adapted and shaped for oral admittance into the gastrointestinal tract for extended residency in the stomach of the gastrointestinal tract as an in vivo reservoir for the controlled delivery of a beneficial orally administrable drug to the gastrointestinal tract for executing a therapeutic program in the gastrointestinal tract, said body comprising:
  (2) a pharmaceutically acceptable non-toxic, non-hydrated cellulose gum that exhibits the ability to retain fluid within its cellulose gum structure, absorb fluid from the gastrointestinal tract, and expand with at least a 2 fold volume increase for retaining the dispensing device in the stomach over an extended period of time;
  (3) a plurality of tiny pills dispersed throughout said body comprising the non-hydrated cellulose gum, the tiny pills comprising:
    (a) a dosage amount of a beneficial orally administrable drug; and,
    (b) a wall comprising a release rate controlling composition comprising a cellulosic polymer that is different than the body comprising the non-hydrated cellulose gum, which wall surrounds the dosage amount of drug; and,
  (4) wherein, when the dispensing device is in the gastrointestinal tract fluid environment of use, the device executes the therapeutic program for imparting a beneficial effect by (c) tiny pills delivering drug in the stomach for absorption in the stomach and for passage into the intestine for absorption in the intestine, and by (d) the body comprising the hydrated cellulose gum releasing tiny pills for passing into intestine with the tiny pills delivering drug over a period of time.

* * * * *